(12) United States Patent
Stockel et al.

(10) Patent No.: US 6,426,064 B1
(45) Date of Patent: Jul. 30, 2002

(54) HAIR TREATMENT COMPOSITIONS

(76) Inventors: Richard F. Stockel, 475 Rolling Hills Rd., Bridgewater, NJ (US) 08807; Robin Davidson, 3084 Pfefferkorn Rd., West Friendship, MD (US) 21794

( * ) Notice: Subject to any disclaimer, the term of this patent is extended or adjusted under 35 U.S.C. 154(b) by 0 days.

(21) Appl. No.: 09/478,273

(22) Filed: Jan. 5, 2000

(51) Int. Cl.⁷ ................................................. A61K 7/06
(52) U.S. Cl. ................... 424/70.11; 424/70.1; 424/401
(58) Field of Search ................................. 424/401, 70.1, 424/70.11, 70.17

(56) References Cited

U.S. PATENT DOCUMENTS

| | | |
|---|---|---|
| 3,683,939 A | 8/1972 | Johnsen |
| 4,186,188 A | 1/1980 | Gumprecht |
| 4,638,822 A * | 1/1987 | Grollier et al. |
| 4,793,992 A | 12/1988 | Mathews |
| 5,811,086 A * | 9/1998 | Matsuzawa et al. |

FOREIGN PATENT DOCUMENTS

| | | | |
|---|---|---|---|
| DE | 19839569 A1 | * | 3/2000 |
| JP | 406157237 A | * | 6/1994 |
| JP | 408041445 A | * | 2/1996 |

\* cited by examiner

Primary Examiner—Thurman K. Page
Assistant Examiner—Brian K. Seidleck

(57) ABSTRACT

Cosmetic compositions containing in a mostly aqueous medium, a highly charged anionic water-soluble polymer and a polyamino acid, and their use in the treatment of keratinous materials.

4 Claims, No Drawings

HAIR TREATMENT COMPOSITIONS

INVENTION BACKGROUND

The external keratin tissue, which represents the protective covering of the human body, encompassing hair, skin, and nails. Keratinous tissues are normally acidic, having isoelectric points on the acidic side of the pH scale. Acidity causes the amino acid cystine, which has a disulfide bond to cleave with concomitant lose in the tensile strength of hair.

A well know method for improving the cosmetic feel and appearance of hair is to treat it with compositions contain polypeptides obtained from partial hydrolysis of collagen, wheat protein, or wheat starch and the like. U.S. Pat. Nos. 3,683,939; 4,186,188, and 4,793,992 teach this prior art.

High molecular weight anionic polymers, like polystyrene sulfonate are also know in the prior art as cosmetic ingredients. National Starch and Chemical Company describes the use of such a product known as Flexan® 130.

It is an ionic polymer with excellent electrical conductivity. Films made from this polymer are hard, tough, but water-soluble.

SUMMARY OF THE INVENTION

It has now been unexpectedly found that certain cosmetic preparations for treatment of keratinous tissue containing polymeric aspartic acid and polystyrene sulfonate have unique properties for the treatment of hair. Specifically these cosmetic preparations comprise aqueous solutions having a pH range of about 5 to about 9.

The molecular weight of polyaspartic acid can range from about 2,000 to about 50,000. The sodium salt of polystyrene sulfonate should have a molecular weight range of about 15,000 to about 500,000.

Keratinous tissue treated with cosmetic preparations embodying features of this invention exhibit cosmetic characteristics including excellent anti-static properties, improved manageability, body and sheen, improved curl retention and does not impart stickiness, greasiness or build-up problems.

DESCRIPTION OF THE INVENTION

This invention teaches cosmetic compositions, which are useful for treating keratinous, tissue, particularly hair. For the most part these are aqueous solutions of polyamino acids and high molecular weight anionic polymers having acidic functionality's, or salts thereof.

These unique compositions can be altered through the use of a variety of additives. Alcohols, silicones, water-soluble thickeners, plasticizers, surfactants, humectants, lubricants, proteins, and other modifiers can be added to achieve a desired effect. Anyone skilled in the art of cosmetic formulations can decipher which ingredients are required for a particularly property. In general, none of these additives, at low concentrations will detract from the desired properties of the novel combination obtained by the teachings of this invention.

There are several variables which have been found to be important to achieve optimum results, which consist of excellent anti-static properties, even at very low humidity, improved manageability, body and sheen, curl retention, no stickiness or greasiness or build-up problems.

The combination of these two polymeric materials in aqueous solution can tolerate a wide range of pH from about 5 to greater than 9. A preferred range would be from about 7 to about 9.

The concentration of the two active polymers is also important. If too little <0.5 wt. % is used the desired effects are minimized, while higher concentrations >6 wt. % an undesirable stiffness imparted to the hair fibers will result. The preferred range of concentration for each ingredient is from about 0.5 to about 3.5 wt. %.

A third variable is molecular weight. The polyamino acid is the lower molecular weight polymer. It can range from about 1,000 to about 50,000. The preferred range is from about 2,000 to about 20,000. In contrast and unexpectedly, the molecular weight of the acidic anionic polymer can range from 25,000 to about 500,000 with a preferred range of about 50,000 to about 200,000.

What is quite novel and unexpected with the cosmetic compositions of this invention is the fact that our polymeric compositions have a significant anionic nature even at a pH of 6 (Determined by FTIR). This is particularly true when the polyamino acid is polyaspartic acid. There are several forms of polyaspartic acids, generally known as alpha, beta or gamma. All of these structural modifications are acceptable for the teachings of this invention. A particularly desirable polyaspartic acid is available commercially. It is called Donlar A-3C (Donlar Corporation, Bedford Park, Ill.). It has a molecular weight of 3,000.

A preferred strong anionic polymeric material which functions within the scope of this invention is available commercially. It is known as Flexan® 130 (National Starch and Chemical, Bridgewater, N.J.). It's molecular weight is approximately 130,000.

EXAMPLES

It has been found by trial and error, that the two unique polymeric active ingredients in this invention can be used at concentrations of from about 0.5 to about 3.5 weight % each, in any given formulation.

Obviously, a formulation can be maximized depending on the relative humidity and hair texture all within this concentration range.

Using the following basic formulation, the results of hundreds of tests are summarized.

| | |
|---|---|
| 3.5 weight % | Flexan ® 130 |
| 1.5 weight % | Donlar ® A-3C |

I. Static electricity is problematic for styling hair ranging from very severe to slight interference depending on several conditions:
 1. Climatic Conditions: (indoors or outdoors) Static is more intense in a dry atmosphere and negligible in a humid environment.
 2. Blow Styling: (universally used) Creates static in all types of hair in any type of environment (less when humid, more when dry).
 3. Hair Texture: All textures are affected by static electricity but fine hair seems to be most affected.

II. Tested on hundreds of people in a professional salon on all types of hair in a wide range of climactic conditions.
 1. Static Control: Eliminates all static electricity until shampooed out. Tested by clients at home on a daily basis for a few weeks, as well as in a salon on a daily basis over several months.
 2. Humidity Control: All types of hair become resistant to humidity until shampooed out. Tested in the salon on a daily basis for several months and by salon clients at home for about two weeks each, on a daily basis. Results were recorded on a daily basis by each client. a. Straight Hair-(especially fine texture) does not go limp and flat even in high humidity. b. Curly Hair-styled straight does not revert back to curl or frizz in high humidity.

3. Mousse or Gel Characteristics: acts like a mousse or gel but is much lighter, almost weightless (mousses and gels are heavy, sticky by comparison) leaving the hair feeling cleaner, softer, and fuller until shampooed out.
4. Gloss and Shine: produces an excellent gloss that only other products specially designed for shine can compare to, but does not leave the hair limp or develop build-up.
5. Build-Up: many products develop a coating on the hair that has to be removed by a special shampoo, this leaves no build-up at all.

FURTHER TESTS

Using a formulation with each of the two polymeric materials at a 2.50 weight % level, three women tested this product for one week. The properties sort were anti-static, improved manageability, body, and sheen, curl retention, no stickiness or greasiness, and a minimal build-up. The treated hair was all blown-dry.

| Level of Humidity | Effectiveness<br>1 (low) to 10 (high) |
|---|---|
| Subject I<br>Type of Hair-fine, wavy, and curly | |
| low | 9 |
| low | 10 |
| medium | 8 |
| high | 8 |
| high | 9 |
| high | 9 |
| medium | 10 |
| Level of Humidity | Effectiveness |
| Subject II<br>Type of Hair-medium texture, curly and color treatment | |
| high | 10 |
| medium | 10 |
| medium | 10 |
| low | 10 |
| low | 10 |
| low | 10 |
| low | 10 |
| Level of Humidity | Effectiveness |
| Subject III<br>Type of Hair-medium texture, straight | |
| low | 10 |
| low | 10 |
| low | 10 |
| low | 10 |
| low | 10 |
| medium | 9 |
| high | 8 |

What is claimed is:

1. A composition for treating hair to impart anti-static property, and improve manageability which comprises applying to the hair an aqueous solution having a pH from about 5 to about 9, said aqueous solution containing both a salt of polyaspartic acid, and a salt of polystyrene sulfonate each being present in a concentration range of from 0.5 to about 3.5 weight percent, and furthermore said aqueous solution having both salts present primarily in the anionic form.

2. The composition of claim 1 in which the salt of polyaspartic acid is in an alpha, beta, or gamma structural form.

3. The composition of claim 1 in which the salt of polyaspartic acid has a molecular weight of about 2,000 to about 50,000.

4. The composition of claim 1 in which the salt of polystyrene sulfonate has a molecular weight of about 50,000 to about 500,000.

* * * * *